US012027653B2

(12) United States Patent
Riemer et al.

(10) Patent No.: US 12,027,653 B2
(45) Date of Patent: Jul. 2, 2024

(54) LED/LD ILLUMINATION DEVICE WITH SEPARATE LUMINOPHORE CONFIGURATION, AND METHOD FOR PRODUCING SAME

(71) Applicants: Tridonic Jennersdorf GmbH, Jennersdorf (AT); W&H Dentalwerk Bürmoos GmbH, Bürmoos (AT)

(72) Inventors: Steffen Riemer, Krottendorf-Gaisfeld (AT); Franz Schrank, Raaba (AT); Patrick Uitz, Fehring (AT); Wilhelm Brugger, Wals-Siezenheim (AT); Thomas Irran, Salzburg (AT)

(73) Assignees: Tridonic Jennersdorf GmbH, Jennersdorf (AT); W&H Dentalwerk Bürmoos GmbH, Bürmoos (AT)

( * ) Notice: Subject to any disclaimer, the term of this patent is extended or adjusted under 35 U.S.C. 154(b) by 1127 days.

(21) Appl. No.: 16/627,823

(22) PCT Filed: May 24, 2018

(86) PCT No.: PCT/EP2018/063672
§ 371 (c)(1),
(2) Date: Dec. 31, 2019

(87) PCT Pub. No.: WO2019/011511
PCT Pub. Date: Jan. 17, 2019

(65) Prior Publication Data
US 2020/0168772 A1 May 28, 2020

(30) Foreign Application Priority Data
Jul. 13, 2017 (DE) .......................... 102017212030.4

(51) Int. Cl.
*H01L 33/50* (2010.01)
*A61B 5/00* (2006.01)
(Continued)

(52) U.S. Cl.
CPC .......... *H01L 33/507* (2013.01); *A61B 5/0088* (2013.01); *A61B 90/30* (2016.02);
(Continued)

(58) Field of Classification Search
CPC ....... H01L 33/483; H01L 33/58; A61B 90/30; A61C 1/12; F21V 33/0068
See application file for complete search history.

(56) References Cited

U.S. PATENT DOCUMENTS

2003/0025449 A1* 2/2003 Rossner ................ H01L 33/505
257/E33.073
2006/0113906 A1* 6/2006 Ogawa .................. C04B 35/195
257/E33.059
(Continued)

FOREIGN PATENT DOCUMENTS

DE 102005023134 A1 11/2006
DE 102015103331 A1 9/2016
(Continued)

OTHER PUBLICATIONS

First Office Action of JP Application No. 2020-500727 issued by the Japan Patent Office (JPO) on May 31, 2022.
(Continued)

*Primary Examiner* — Jay C Chang
*Assistant Examiner* — Mikka Liu
(74) *Attorney, Agent, or Firm* — Spruson & Ferguson (Hong Kong) Limited

(57) ABSTRACT

The invention relates to an illuminating device (1) comprising a substrate (2), a non-transparent spacer (4) which is connected to the substrate (2) so as to be hermetically sealed, an opening in the spacer (4), opposite said substrate (2), and an illumination element (3) positioned beneath the spacer (4) and beneath the opening, which element is connected to the substrate (2) so as to be hermetically sealed, characterized in
(Continued)

that the opening in the spacer (4) is closed, so as to be hermetically sealed, by an optical element (5) consisting of a glass material the volume of which comprises at least one luminophore and thus constitutes a luminescent composite glass material.

10 Claims, 3 Drawing Sheets

(51) Int. Cl.
- *A61B 90/30* (2016.01)
- *A61C 1/12* (2006.01)
- *C09K 11/77* (2006.01)
- *F21V 33/00* (2006.01)
- *H01L 33/48* (2010.01)
- *H01L 33/58* (2010.01)
- *A61B 1/06* (2006.01)
- *A61C 1/08* (2006.01)
- *F21Y 115/10* (2016.01)

(52) U.S. Cl.
CPC ............ *A61C 1/12* (2013.01); *C09K 11/7787* (2013.01); *F21V 33/0068* (2013.01); *H01L 33/483* (2013.01); *H01L 33/58* (2013.01); *A61B 1/063* (2013.01); *A61B 1/0684* (2013.01); *A61B 2090/304* (2016.02); *A61C 1/088* (2013.01); *F21Y 2115/10* (2016.08)

(56) References Cited

U.S. PATENT DOCUMENTS

| | | |
|---|---|---|
| 2008/0029720 A1 | 2/2008 | Li |
| 2010/0002450 A1 | 1/2010 | Pachler et al. |
| 2011/0002157 A1 | 1/2011 | Shimomura et al. |
| 2012/0107622 A1 | 5/2012 | Borrelli |
| 2014/0140071 A1* | 5/2014 | Daicho ............ C09K 11/77342 362/317 |
| 2016/0139300 A1 | 5/2016 | Cheng et al. |
| 2016/0258582 A1* | 9/2016 | Gindele .................... F21K 9/20 |

FOREIGN PATENT DOCUMENTS

| | | |
|---|---|---|
| JP | 2008-258214 A | 10/2008 |
| JP | 2008-541465 A | 11/2008 |
| JP | 2013-254972 A | 12/2013 |
| JP | 2015-3025 A | 1/2015 |
| JP | 2016-164880 A | 9/2016 |
| WO | 2006097876 A1 | 9/2006 |
| WO | 2013011075 A2 | 1/2013 |
| WO | 2014178515 A1 | 11/2014 |

OTHER PUBLICATIONS

Office Action of CN2018800386215 issued from the China National Intellectual Property Administration on Oct. 26, 2022.

* cited by examiner

LED/LD ILLUMINATION DEVICE WITH SEPARATE LUMINOPHORE CONFIGURATION, AND METHOD FOR PRODUCING SAME

FIELD OF THE INVENTION

The invention relates to an illuminating device on the basis of light emitting diodes (LEDs) or laser diodes (LDs) with a novel hermetically sealed remote luminescent configuration in the form of an optical element (e.g., a lens) made of a glass material whose volume comprises luminescence material and as such is suitable for superheated steam sterilization and to a method for producing the same, wherein "luminescent substance" is understood to mean a luminescent material hereinafter.

BACKGROUND

Previously known illuminating devices with remote luminescent configurations of this type are miniaturized LED modules, which are also used in a ring-shaped arrangement, for example in medical instruments, such as medical, in particular dental, handpieces or contra-angle handpieces. Hermetically sealed designs are produced, for example, in the following way (see DE102015103331B4).

On a basis (a base or holder, referred to as a substrate hereinafter) made of ceramic or metal, blue emitting LED chips are mounted and a spacer in the form of a metal cap with one or more windows made of transparent glass is soldered or welded thereon. However, prior to the connection to the substrate, a converter is glued as a thin element onto the inside of the transparent window. The principle is always that an air space is adjacent to the LEDs, a remote luminescent film is arranged at a distance, and above this film is arranged with a transparent lens.

In the case that luminescent particles are described in a matrix of glass in the prior art, it only concerns applied, glued or sintered layers on a glass (or ceramic) carrier, all of which are not suitable for producing a hermetically sealed LED arrangement.

For example, in US20120107622A1, the luminescent layer is applied to a glass plate in a type of sintering process.

US20080029720A1 describes a luminescent layer in an organic binding agent, similar to a lacquering or coating.

WO2006097876 discloses luminescent layers in a ceramic matrix.

WO2014178515A1 relates to coated molded parts made of glass, luminescent particles similar to the previous documents in a glass matrix.

In US20110215701, various binding agents and light-scattering additives are listed within the framework of coating a carrier with a luminescent substance.

US20100002450A1 describes a lens holder based on a mechanical fixing. Color conversion or luminescent substance is not mentioned in this document.

The process for achieving a hermetically sealed arrangement based on illuminating devices of the construction types listed above is time-consuming, expensive and still fraught with problems. For example, the gluing of the converter on the window can fail or the height of the spacer (the metallic cap) cannot be reduced further because the converter (the converter element) is typically 200 μm thick. All solutions which are specified in the prior art and which describe dispersed luminescent particles in a glass or ceramic matrix prove to be unsuitable for producing a hermetically sealed connection with a metallic molded body.

In summary, adhesions or coatings with plastics, which are currently the prior art in this field, do not result in the sealed design according to the present invention, which is required for a desired superheated steam sterilization and temperature shock resistance required in medical use.

SUMMARY OF THE INVENTION

The present invention is therefore based on the object of simplifying an illuminating device of this type in order to create a robust and reliable design for the remote luminescent element in a hermetically sealed design suitable for the superheated steam sterilization for medical use, as well as of specifying a method of how such a device can be produced easily and cost-effectively.

This object is achieved by the features of the independent claims. Advantageous developments of the invention are described in the related subclaims.

DETAILED DESCRIPTION

The basic idea of the present invention is to combine the previously separate arrangement of an optical component (e.g., transparent lens) and a remote luminescent film in a single component so that the luminescent substance is dispersed in the glass material of the optical component (e.g., a lens), i.e., is homogeneously fused thereto, which does not only result in better thermal properties but generally proves to be more stable and more durable.

Figure 1:
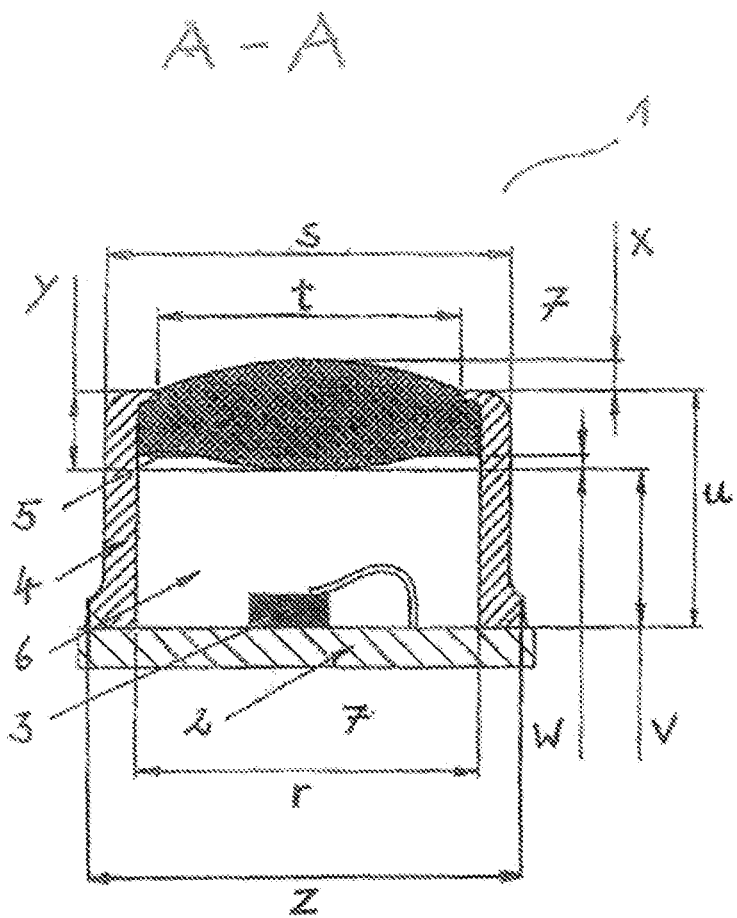
FIG. 1 shows the device according to the present invention in a sectional view A-A.
Figure 2:
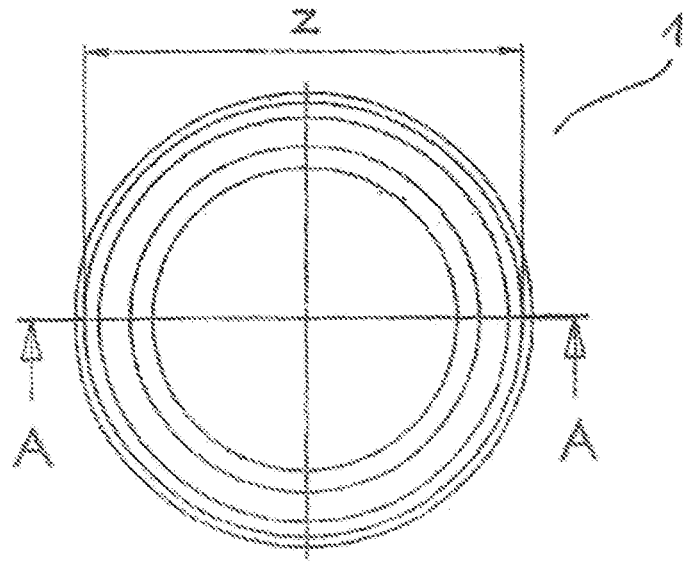
FIG. 2 shows the top view of such a device.

FIG. 1 shows a sectional view A-A of the illuminating device 1 according to the invention. FIG. 2 shows a top view of this device.

A preferably non-transparent substrate 2, for example made of ceramic, forms the basis for the illuminating device 1 according to the invention. On this substrate 2 is firmly mounted the illuminating element 3, an LED element or a laser diode. The illuminating element 3 may in this case be designed as an integrated circuit or SMD component (Surface Mounted Device). The electrical connections of the illuminating element 3 are guided in a hermetically sealed manner through the substrate, e.g., through a metallic through-connection also burnt into the ceramic or through a fused glass feed-through. On substrate 2 is additionally located a non-transparent spacer 4, which supports at a distance to the substrate surface in an opening a lens or a diffuser disk (a diffusion disk) or a different optical element 5, which is referred to below as such. The distance is dimensioned such that an air space 6 is formed between the optical element and the substrate 2, said air space being able to easily accommodate the illuminating element 3. The spacer 4 is advantageously made of metal and cylindrical and, together with the optical element 5 supported by it, forms a cap that closes the illuminating element 3 in a hermetically sealed manner off from the outer chamber 7. This hermetic sealing of the air space 6 toward the outer chamber 7, which is extraordinarily important for the invention, is achieved on the one hand by soldering or welding of the spacer 4 with the substrate 2, on the other hand by fusing or casting of the optical element 5 to/with the spacer 4 in the region of the opening at very high temperature. The likewise hermetic sealing of the electrical connections of the illuminating element 3 through the substrate 2 was already described.

Also essential for the present invention is the integration of the previously independent converter element into the optical element 5, whereby the complexity of the device is reduced on the one hand and the reliability, especially with regard to autoclavability and temperature shock resistance, is significantly increased on the other hand. The time-consuming assembly step for a color conversion element is dispensed with. Instead of a previously used transparent, colorless glass, a luminescent glass composite material is used as optical element 5 (as already mentioned, the term "luminescent substance" is to be understood in this context as luminescent/luminous material). For this purpose, in the production process described below, the glass powder is mixed homogeneously with the luminescent particles and fused to the opening of the spacer.

If necessary, additional light-scattering additives (e.g., $Al_2O_3$ or $TiO_2$) or additional excipients can be added, the latter in order to, for example, prevent separation of dye particles from the glass matrix in further process steps or to adjust the viscosity of the matrix by means of filler particles. However, the preferred embodiment of the invention is the pure homogeneous dispersion of the luminescent particles in the glass material of the optical element 5.

The production method for the illuminating device 1 described just now is as follows:

First, a hermetically sealed connection between spacer 4 and glass composite material optical element 5 is produced. This step may take place in two ways.

Variant 1:
By melting the glass powder with the luminescent particles mixed homogeneously therein and possibly additional additives, a rod-shaped composite glass body is produced.

Glass panes of a desired thickness are separated from this glass body. The separated glass pane is inserted into the opening of the spacer 4 and, at approx. 1000° C. (900-1200° C.) fused thereto or cast therewith in a sealed manner in the region of the opening under protective gas.

Variant 2:
The glass powder is pressed with the luminescent particles mixed homogeneously therein and possibly additional additives to form a tablet.

The tablet is inserted into the opening of the spacer 4 and, at approx. 1000° C. (900-1200° C.) fused thereto or cast therewith in a sealed manner in the region of the opening under protective gas.

For example, a lens shape of the optical element 5 can thus result from the surface tension of the liquid glass composite. For both variants, other (lens) shapes can also be achieved by suitable measures (e.g., by molding trays).

Then, the illuminating element 3 is attached to the substrate 2 in a hermetically sealed manner and the electrical lines of the illuminating element 3 through the substrate 2 are sealed hermetically by means of a glass feed-through or a metallic through-connection.

Lastly, the substrate 2 is likewise connected to the spacer 4 by soldering or welding (for materials that are too different and difficult to connect, e.g., metal/ceramic, preferably by laser welding).

It should be emphasized once again that the luminescent particles in the volume of the optical element (e.g., a glass lens) cast in one piece are exclusively homogeneously distributed by the procedure described above, in contrast to a popular prior art method, in which a luminescent layer is sintered onto a glass body (as described in US 20120107622A1).

Adhesive connections are also not necessary (e.g., gluing a luminescent film onto the optical element in the prior art, the film being the component which is the least temperature-stable) and the attachment of a pre-finished luminescent substance/glass body without subsequent fusing process, which would greatly reduce the desired thermal stability of the device. The aforementioned possibility of using a powerful laser diode (LD) as illuminating element 3 is also possible due to the high thermal stability of the entire system.

As the melting process or the fusing process of the luminescent glass body requires relatively high temperatures, which may potentially impair the efficiency of the luminescent substance, luminescent substances that are very temperature-stable and are therefore particularly suitable for the invention are proposed. These substances are yellow and green emitting garnets, such as YAG: $Ce^{3+}$, LuAG. $Ce^{3+}$, red emitting oxides, such as $Y_2O_3$: $Eu^{3+}$, or oxynitride-based/nitride-based red luminescent substances (e.g., $SrAlSi_4N_7$: $Eu^{2+}$, $(Ca,Sr)AlSi_4N_7$:$Eu^{2+}$, CaSiAlON:$Eu^{2+}$, CaAlSi$(ON)_3$:$Eu^{2+}$, $CaAlSiN_3$:Eu or $(Ca,Sr)AlSiN_3$:Eu) with a homogeneous volume distribution of 5 to 40 vol. % but preferably between 10 and 25 vol. % in individual or total concentration. Depending on the desired color temperature of the emitted white light, luminescent mixtures with 2 or 3 luminescent substances can be used in due consideration of the mentioned total concentrations. Advantageously, the total concentration of the luminescent substances of 40 vol. % should not be exceeded. Spherical (ball-shaped) particles with a smooth surface are particularly advantageous in this application. The average grain size of the used luminescent substances (the so-called $d_{50}$ value) is between 2 and 20 μm, preferably between 5 and 18 μm.

In the case of a cylindrical illuminating device 1 of the present invention and a lens as optical element 5, the following orders of magnitude are provided with regard to use in dentistry or endoscopy:

(r) Diameter of the lens=inner diameter of the spacer: 0.5-10.0 mm, e.g., 1.73 (+0.04;−0.01) mm;
(s) Outer diameter of the spacer: 1.0-15 mm, e.g., 2.05 (+0.02;−0.05) mm;
(t) Diameter of the opening: 0.5-10.0 mm, e.g., 1.53 mm;
(u) Height of the spacer: 0.5-5 mm, e.g., 1.20 (±0.10) mm;
(v) Height of the air space: 0.01-4.8 mm, e.g., 0.70 (+0.17; 0.00) mm;
(w) Inside lens curvature: 0-+/−5 mm, e.g., 0.07 mm maximum;
(x) Outside lens curvature: 0-+/−5 mm, e.g., 0.15 (0.00;−0.20) mm;
(y) Inside lens curvature to upper edge of the spacer: e.g., 0.40 (0.00; −0.10) mm;
(z) Diameter of upper outer edge of the weld/solder groove: 1.0-15 mm, e.g., 2.20 (±0.10) mm.

In addition, studies in the context of the development of the illuminating device according to the invention have shown that a thickness of the glass composite material of between 0.2 and 1.0 mm, preferably between 0.4 and 0.8 mm, seems to be optimal for the above dimensions.

In the case of such a dimensioning of the illuminating device 1 according to the invention and hermetic sealing according to the method described above, leakage rates of less than $10^{-8}$ mbar*liter/second can be achieved in the air space of the illuminating device, which, as already mentioned, enables stable autoclavability and temperature shock resistance. Designs in other orders of magnitude (e.g., in the submillimeter range or in the centimeter range) for other applications and areas of use are not excluded.

The autoclavability, i.e., the suitability for superheated steam sterilization, and a high temperature shock resistance should also be ensured in that the materials of all components of the device according to the invention and their interconnections are selected and/or designed accordingly.

The illuminating device 1 can also be designed as a ring light or in the form of related structural shapes, wherein the transparent optical element 5 made of luminescent glass composite material can have a curvature on one or both sides.

Accordingly, the spacer 4 can have several (possibly radially symmetrically arranged, differently sized) openings, which are respectively closed in a hermetically sealed manner by a suitable optical element 5, and wherein an illuminating element 3, which is attached in a hermetically sealed manner to the substrate, corresponds to each opening/optical element combination, and wherein the optical elements 5 and the illuminating elements 3 of the various openings may absolutely be different.

FIGS. 3 to 6 show how the illuminating device 1 according to the invention can be used, for example, in dental technology.

The medical, in particular dental, handpiece 8 comprises a handle part 9 and a head part 10 arranged at an angle thereto. In the head part 10 is arranged a movable, preferably rotating, tool holder or tool opening 13, in which a tool 14, e.g., a rotatable drill, can be accommodated. This tool can be unlocked by pressing a push button 11, for example, and removed again.

Figure 3:
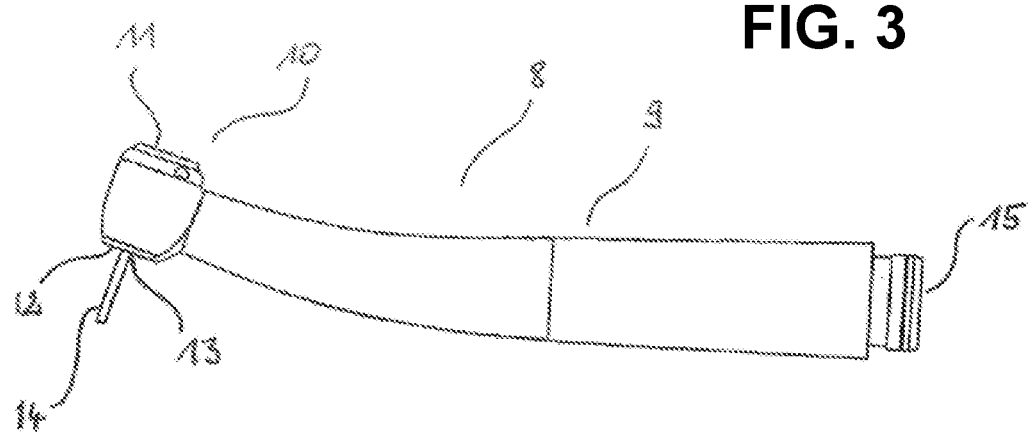
FIG. 3 shows a medical instrument in the form of a dental handpiece or contra-angle handpiece.

In the case of FIG. 3, the tool 14 thus protrudes at an angle to the longitudinal axis of the handle part 9 from the head part 10. The tool 14 is driven by at least one drive element and, as such, is connected to the tool 14. In this case, the drive element is preferably designed as a rotating shaft. Depending on the type of the handpiece 8, the drive element can comprise additional or alternative components, such as one or more additional rotating or oscillating shafts, one or more gears or gear units, a motor, a pneumatically drivable rotor, a vibration generator, etc. At the end of the handle part 9, the dental handpiece has a connection 15 which can be used to supply the head part 10 with fluids or media needed for driving (e.g., water, compressed air, electrical current, etc.).

The illuminating device according to the invention can, for example, be used in two ways: individually or in the shape of a ring.

Figure 4:
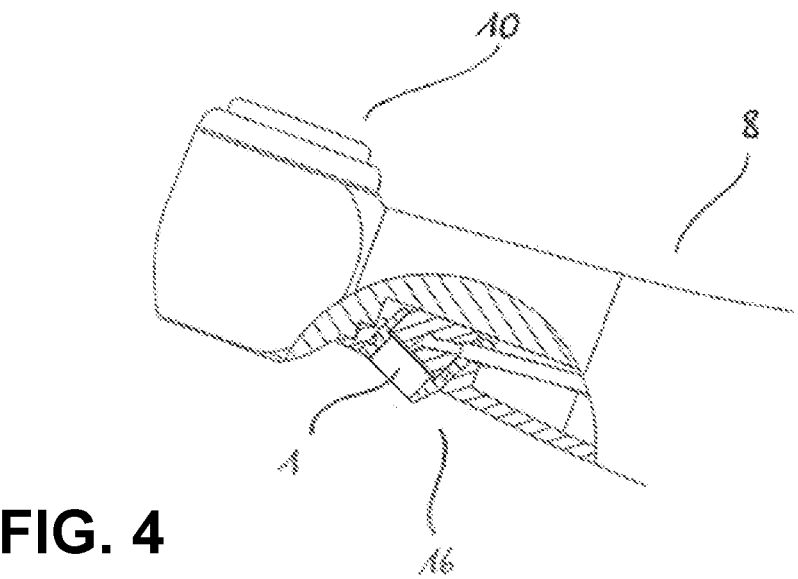
FIG. 4 shows the front part of the medical instrument with an individual illuminating device.

According to FIG. 4, illumination 16 takes place individually, namely in that only a single illuminating device 1 according to the invention is integrated into the end of the handle part 9 facing the head part 10, and the delivery of a bundled light beam to the work area of a treatment site is thus effected. The illuminating device 1 is in this case located in a light output opening of the outer sleeve of the handpiece 8.

Figure 5:
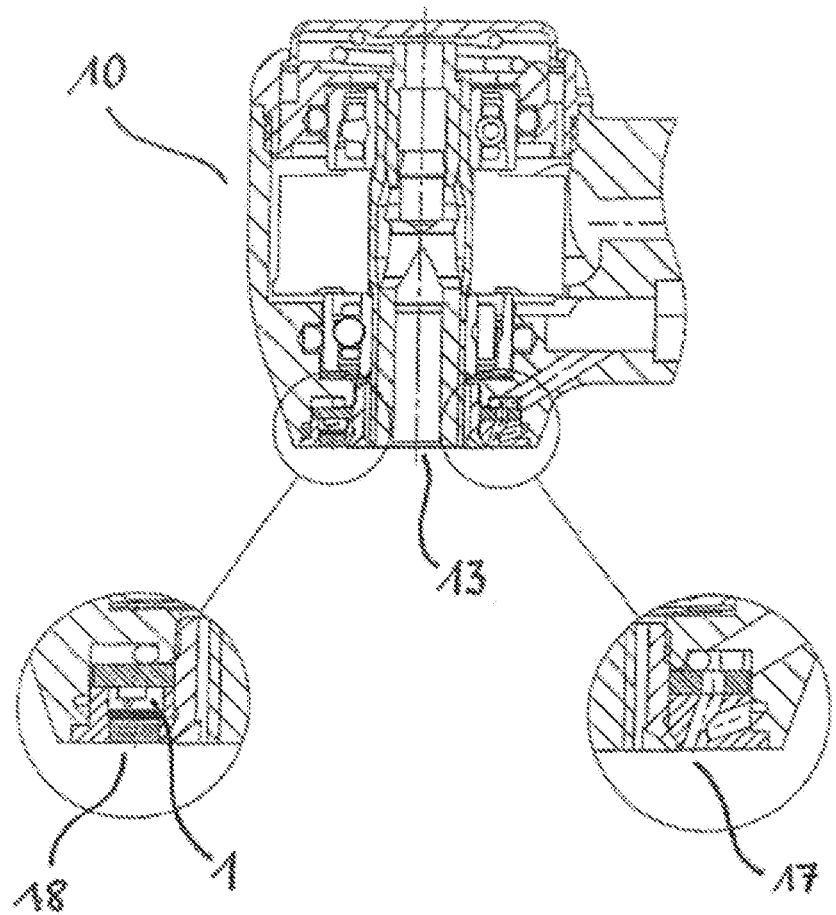
FIG. 5 shows the head end of a dental handpiece or contra-angle handpiece with a ring-shaped illuminating device in a sectional view B-B.
Figure 6:
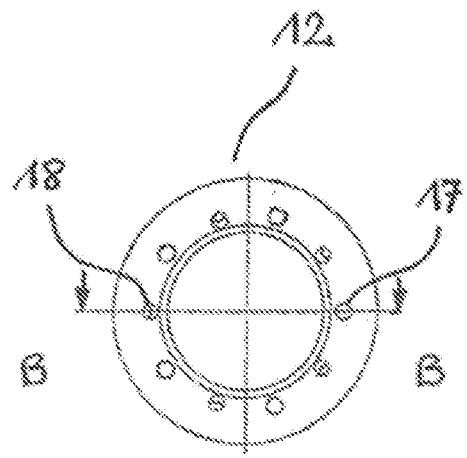
FIG. 6 shows the top view of the head end of the dental handpiece or contra-angle handpiece with the ring-shaped illuminating device.

According to FIGS. 5 and 6, illumination 18 takes place in the shape of a ring by means of a ring-shaped fluid and radiation output end 12, through which both radiation (e.g., light) and fluid (e.g., water, compressed air, etc.) can be introduced into the work area of a treatment site.

FIG. 5 shows in a sectional view the head end 10 of the dental instrument 8, in the center of which head end is arranged the tool opening 13. In this sectional view, a radiation output opening 18, in which the illuminating device 1 according to the invention is accommodated, is located on the left side of the tool opening 13. On the right side of the tool opening 13 is located a fluid output opening 17 into which several fluid channels open in order to be able to output various fluids (e.g., water and compressed air) individually or as a mixture. FIG. 6 shows that radiation output openings 18 and fluid output openings 17 are arranged alternately on the ring-shaped fluid and radiation output end 12 in order to achieve a certain homogeneity of the radiation or fluid output.

A detailed description of the dental instrument with ring-shaped illumination is disclosed in WO 2013011075.

LIST OF REFERENCE SIGNS

1 Illuminating device (according to the invention)
2 Substrate
3 Illuminating element
4 Spacer
5 Optical element (e.g., lens)
6 Air space
7 Outer chamber
s Outer diameter of the spacer
t Diameter of the opening
u Height of the spacer
v Height of the air space
w Inside lens curvature
x Outside lens curvature
y Inside lens curvature to upper edge of the spacer
z Diameter of upper outer edge of the weld/solder groove
8 Dental instrument or handpiece
9 Handle part
10 Instrument head or head part
11 Push button
12 Ring-shaped fluid and radiation output end
13 Tool opening
14 Tool
15 Connection
16 Individual illumination
17 Fluid output opening
18 Radiation output opening

What is claimed is:

1. A method for producing an illuminating device, wherein the illuminating device comprises a substrate, a non-transparent spacer connected to the substrate in a hermetically sealed manner, an opening opposite the substrate in the spacer, and an illuminating element located under the spacer and under the opening and connected to the substrate in a hermetically sealed manner, wherein the opening of the spacer is closed in a hermetically sealed manner with an optical element made of a glass material, a volume of the optical element comprising at least one luminescent substance such that the glass material is a luminescent glass composite material, and wherein the method comprises the following steps:

producing a hermetic connection between the spacer and the optical element:

Variant 1: A) producing a rod-shaped glass body by melting a glass powder with luminescent particles mixed homogeneously therein and any additives;

B) separating glass panes of a desired thickness from the glass body;
C) inserting the glass pane into the opening of the spacer;
D) fusing in a sealed manner under a protective gas at a temperature between 900° ° C. to 1200° C.;

or

Variant 2: a) pressing a glass powder with luminescent particles mixed homogeneously therein and any additives;
b) inserting a tablet into the opening of the spacer;
c) fusing in a sealed manner under a protective gas at a temperature between 900° ° C. to 1200° C.;

attaching the illuminating element to the substrate in a hermetically sealed manner and hermetically sealing electrical lines of the illuminating element through the substrate by means of a glass feed-through or metallic through-connection; and connecting in a hermetically sealed manner the substrate to the spacer by soldering or welding.

2. The method according to claim 1, wherein:
the optical element is brought into a specific form by suitable mold elements during each of the fusing steps D) and c).

3. An illuminating device produced by the method of claim 2.

4. A medical instrument comprising the illuminating device of claim 3.

5. A dental handpiece comprising the illuminating device of claim 3.

6. A contra-angle handpiece comprising the illuminating device of claim 3.

7. An illuminating device produced by the method of claim 1.

8. A medical instrument comprising the illuminating device of claim 7.

9. A dental handpiece comprising the illuminating device of claim 7.

10. A contra-angle handpiece comprising the illuminating device of claim 7.

* * * * *